United States Patent
Mieno

(10) Patent No.: US 10,145,781 B2
(45) Date of Patent: Dec. 4, 2018

(54) METHOD OF ESTIMATING FRICTIONAL RESISTANCE OF SHIP BOTTOM COATING FILM, AND A METHOD OF EVALUATING COATING FILM PERFORMANCE USING SAID METHOD AND A DEVICE FOR EVALUATING COATING FILM PERFORMANCE

(71) Applicant: CHUGOKU MARINE PAINTS, LTD., Otake-shi (JP)

(72) Inventor: Hirohisa Mieno, Otake (JP)

(73) Assignee: CHUGOKU MARINE PAINTS, LTD., Otake-shi (JP)

( * ) Notice: Subject to any disclaimer, the term of this patent is extended or adjusted under 35 U.S.C. 154(b) by 725 days.

(21) Appl. No.: 14/391,259

(22) PCT Filed: Mar. 4, 2013

(86) PCT No.: PCT/JP2013/055777
§ 371 (c)(1),
(2) Date: Oct. 8, 2014

(87) PCT Pub. No.: WO2013/153877
PCT Pub. Date: Oct. 17, 2013

(65) Prior Publication Data
US 2015/0081231 A1    Mar. 19, 2015

(30) Foreign Application Priority Data
Apr. 9, 2012    (JP) .................................. 2012-088427

(51) Int. Cl.
*G06F 19/00* (2018.01)
*G01N 19/02* (2006.01)
(Continued)

(52) U.S. Cl.
CPC .............. *G01N 19/02* (2013.01); *B63B 9/001* (2013.01); *C09D 5/16* (2013.01)

(58) Field of Classification Search
CPC ......... B23K 2203/50; B22F 2003/1054; B22F 2003/1056
(Continued)

(56) References Cited

U.S. PATENT DOCUMENTS 6,516,652 B1    2/2003    May et al.
6,828,030 B2    12/2004    Arimura et al.
(Continued)

FOREIGN PATENT DOCUMENTS

CN    1645050 A    7/2005
CN    101050958 A    10/2007
(Continued)

OTHER PUBLICATIONS

International Search Report dated May 21, 2013, in PCT/JP2013/055777, filed Mar. 4, 2013.
(Continued)

*Primary Examiner* — Edward Raymond
(74) *Attorney, Agent, or Firm* — Oblon, McClelland, Maier & Neustadt, L.L.P.

(57) ABSTRACT

A method of estimating a frictional resistance of a ship bottom coating film, the method including measuring any one of Rz (maximum height roughness), Rc (mean height of roughness profile elements), Ra (arithmetic mean roughness), Rq (root mean square roughness) and RZJIS (ten-point mean roughness) as a roughness height R in a mean length RSm of roughness profile elements in the range of 2,000 to 10,000 μm according to JIS B 0601:2001 (ISO4287:1997) on a coating film formed by applying a ship bottom coating paint on a substrate and calculating a frictional resistance increase rate FIR (%) from a mirror surface
(Continued)

by the following formula (1), wherein coefficient C is a constant depending on the kind of the roughness height R and a frictional resistance testing method, and is previously determined in such a manner that plural ship bottom coating films each having different roughness are subjected to a roughness measurement and a frictional resistance test in a definite evaluation length, and then the coefficient C is determined by the formula (1) using the roughness height R, the mean length RSm of roughness profile elements and the frictional resistance increase rate FIR (%), which have been measured.

20 Claims, 5 Drawing Sheets

(51) Int. Cl.
    *C09D 5/16*     (2006.01)
    *B63B 9/00*     (2006.01)

(58) Field of Classification Search
    USPC ........................ 702/41–45, 182–185
    See application file for complete search history.

(56) References Cited

U.S. PATENT DOCUMENTS

| | | | |
|---|---|---|---|
| 6,939,925 | B2 | 9/2005 | Sakamoto et al. |
| 6,958,366 | B2 | 10/2005 | Tokunaga et al. |
| 2002/0011177 | A1 | 1/2002 | Yamamori et al. |
| 2004/0029997 | A1 | 2/2004 | Yamamori et al. |
| 2006/0045863 | A1 | 3/2006 | Haeffner et al. |
| 2009/0053166 | A1 | 2/2009 | Niimoto |
| 2010/0222452 | A1 | 9/2010 | Kawahara |
| 2012/0029888 | A1 | 2/2012 | Horng et al. |
| 2015/0132539 | A1* | 5/2015 | Bailey ............ C23C 16/34 428/141 |

FOREIGN PATENT DOCUMENTS

| | | |
|---|---|---|
| CN | 101050959 A | 10/2007 |
| EP | 2 368 949 A1 | 9/2011 |
| JP | 60-44568 | 3/1985 |
| JP | 62-39393 | 2/1987 |
| JP | 2-170010 A | 6/1990 |
| JP | 2003-530217 | 10/2003 |
| JP | 2007-2285 A | 1/2007 |
| JP | 4610763 | 1/2011 |
| JP | 4621901 | 2/2011 |
| JP | 4633224 | 2/2011 |
| JP | 4641563 | 3/2011 |
| JP | 4642204 | 3/2011 |
| JP | 4644238 | 3/2011 |
| JP | 4647060 | 3/2011 |
| JP | 4651792 | 3/2011 |
| JP | 4675624 | 4/2011 |
| JP | 4684465 | 5/2011 |
| JP | 4694583 | 6/2011 |
| JP | 4709370 | 6/2011 |
| JP | 4745351 | 8/2011 |
| JP | 4769331 | 9/2011 |
| JP | 4776839 | 9/2011 |
| JP | 4777591 | 9/2011 |
| JP | 4786053 | 10/2011 |
| JP | 4806769 | 11/2011 |
| JP | 4812895 | 11/2011 |
| JP | 4812902 | 11/2011 |
| JP | 4812947 | 11/2011 |
| JP | 4813608 | 11/2011 |
| JP | 4837668 | 12/2011 |
| JP | 4846093 | 12/2011 |
| JP | 2012-7048 | 1/2012 |
| JP | 4884107 | 2/2012 |

OTHER PUBLICATIONS

Hayato Suzuki, et al., "Development of Frictional Resistance Reduction Type Antifouling Paint", Dai 27 Kai Toryo Toso Kenkyu Happyokai Koen Yokoshu, Japan Coating Technology Association, Mar. 9, 2012, pp. 41-45.

Hisao Tanaka, et al., "Influence of Surface Properties of Coatings to Frictional Resistance", Journal of the Kansai Society of Naval Architects, Japan, No. 239, Mar. 25, 2003, pp. 21-27 (with English Abstract).

D. Byrne, "Hull roughness and the impact of outer hull maintenance decisions on ship efficiency", The First International Ship Repair, Spares and Maintenance Conference, 1983, pp. 33-51.

Hideo Sasajima, et al., "Experimental Investigation into Roughness of Hull Surface and Increase of Skin Frictional Resistance", Journal of the Society of Naval Architects of Japan, vol. 117, Jun. 1965, pp. 58-71 (with English Abstract).

Combined Chinese Office Action and Search Report issued Sep. 14, 2015 in Patent Application No. 201380019147.9 (with English translation of Categories of Cited Documents).

Japanese Office Action issued Dec. 8, 2015 in Patent Application No. 2012-088427.

"Geometrical Product Specifications (GPS)—Suface Texture: Profile Method—Terms, Definitions and Surface Texture Parameters" (JIS B 0601, ISO 4287:19997) 2001, 57 Pages (with English Translation).

Hirotomo Ando, et al, "Fundamental Research for Development of a Drag-Reducing Paint for Ship" https://www.nmri.go.jp/main/publications/paper/pdf/21/10/03/PNM21100302-00.PDF, vol. 10, No. 3, Dec. 2010, pp. 245-269 (with English Abstract).

\* cited by examiner

Fig.1 Relationship between frictional resistance increase rate FIR (%) and $Rz^2/RSm$ Fig.2 Relationship between FIR (%) and Rz Relationship between frictional resistance increase rate FIR (%) and RSm Fig. 4 Roughness distribution of a coating film of an actual ship bottom (Replica method/Evaluation length 30 mm)
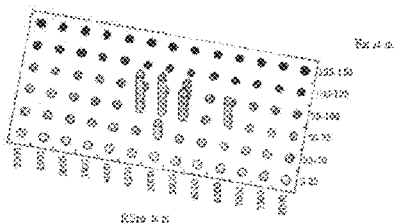
(1) Sample number 15
    Mean Rz = 60.7 μm
    Mean RSm = 4909 μm
    Estimation FIR = 2.0 (%)
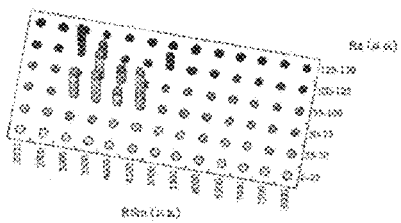
(2) Sample number 15
    Mean Rz = 80.1 μm
    Mean RSm = 3481 μm
    Estimation FIR = 4.8 (%)
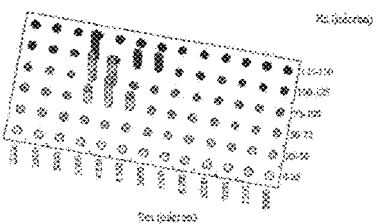
(3) Sample number 12
    Mean Rz = 87.3 μm
    Mean RSm = 3711 μm
    Estimation FIR = 5.4 (%)
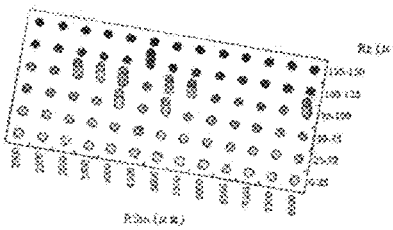
(4) Sample number 9
    Mean Rz = 79.7 μm
    Mean RSm = 4417 μm
    Estimation FIR = 3.8 (%)

Example of roughness acquisition of a coating film of an actual ship bottom

Estimation example of frictional resistance increase rate FIR (%)

METHOD OF ESTIMATING FRICTIONAL RESISTANCE OF SHIP BOTTOM COATING FILM, AND A METHOD OF EVALUATING COATING FILM PERFORMANCE USING SAID METHOD AND A DEVICE FOR EVALUATING COATING FILM PERFORMANCE

TECHNICAL FIELD

The present invention relates to a method of estimating a frictional resistance increase rate of a ship bottom coating film wherein the method can simply and quickly provide evaluation results without individual differences. Furthermore, it relates to a method of evaluating coating film performance simply on a ship bottom coating film of an actual ship and it also relates to an evaluating device.

BACKGROUND ART

As to improvement of a propulsion performance which is the most important item of energy saving measures for ships, the frictional resistance in ship bottom has a major role together with wave-making resistance and viscous pressure resistance.

It is reported that this frictional resistance accounts for 60 to 80 percent of all resistances which a ship receives. The decrease of the frictional resistance is very important for saving the fuel economy of ships.

For ship bottoms, antifouling coating paints are used in order to prevent from attachment of aquatic organism and prevent from deterioration of fuel consumption caused by the aquatic organism attachment. The antifouling coating paints are always applied on the bottom parts where a ship contacts with seawater. Therefore, it is important to prevent increase of the roughness of a coating film surface and thereby decrease the frictional resistance by carrying out a proper coating control or employing an antifouling coating paint having a high smoothing performance in the step of newly building a ship. As such a coating film having antifouling performance and capable of decreasing frictional resistance, there are a self-polishing type coating film, a foul-release type coating film and the like.

It is generally considered that surface roughness is a major factor in the increase of the frictional resistance. Methods of estimating a ship performance from the surface roughness of a coating film has been studied for a long time.

Non patent document 1 discloses a method of evaluating ship performance by roughness of a shop bottom, and a roughness measurement is carried out by a method of using a contact type displacement meter with BSRA roughness meter developed by BSRA (British Ship Building Association). It also discloses that the increase of frictional resistance is calculated from the following numerical formula (1) or (2) based on the roughness measured by this method. These formulas are empirical formulae obtained by measuring surface roughness of an actual ship with BSRA roughness instrument.

$$\Delta C_F \times 10^3 = 105 \left( \frac{k}{L_{pp}} \right)^{\frac{1}{3}} - 0.64 \quad (1)$$

$$\frac{\Delta P_D}{P_D} \times 100\% = 3.8 \times \left\{ (K_2)^{\frac{1}{3}} - (K_1)^{\frac{1}{3}} \right\} \quad (2)$$

In the numerical formula (1), $\Delta C_F$ is an increase of a frictional resistance coefficient, k is a mean roughness height measured by the BSRA roughness instrument and Lpp is a ship length. In the numerical formula (2), $\Delta P_D/P_D$ is an increase rate of supply horsepower, $K_1$ is a roughness height of a ship bottom in an early stage and $K_2$ is a roughness height of the ship bottom in a final stage.

Furthermore, non-patent document 1 discloses that the estimation of using only the roughness height is insufficient and discloses, for example, an evaluation method of using a surface shape parameter t.

$$t = f(\alpha)(\alpha = m_0 m_4 / m_2^2) \quad (3)$$

In the numerical formula, $\alpha$ is a spectrum parameter, $m_0$ is a 0-dimensional spectrum moment, $m_2$ is a 2-dimensional spectrum moment and $m_4$ is a 4-dimensional spectrum moment. As a convenience method, it discloses a method of determining $\alpha$ from $(D_E/D_Z)^2$ ($D_E$ is a shape density of the maximum—the minimum and $D_Z$ is a crossing at 0 point). It furthermore indicates that in the evaluation with the surface shape parameter t, a difference of about ±4% in supply horsepower appears by the difference of the surface shape parameter t even in the same BSRA roughness height (450μ).

Non patent document 2 discloses a relationship of $H^2/\lambda$ wherein H is an apparent wave height (roughness height) and $\lambda$ is an apparent wavelength and frictional resistances in an actual ship and a flat panel test. The roughness height H and the wavelength $\lambda$ used herein are determined by the following procedures (I) to (viii). This method has been used before computer development, the roughness height and wavelength are determined from a sectional profile with working by hand.

(i) Vertical break-lines are drawn for dividing in a horizontally long recoded diagram with a certain constant distance (at first, about 20-50 m in an actual length on an outer plate).
(ii) The maximum point and the minimum point are selected each in each divided section of the recorded diagram.
(iii) The maximum points in the adjacent sections or the minimum points in the adjacent sections are connected respectively to make two sequential line graphs.
(iv) In the vertical break-lines drawn at the beginning procedure, the length of a part that is sandwiched and intercepted between the two sequential lines is taken as an apparent wave height (Hi) of this section. Furthermore, the distance of the first vertical section lines is taken as an apparent wave length ($\lambda$).
(v) In one ship or one specimen steel plate, the apparent wave height H to $\lambda$ is a mean of Hi's in the above procedures.
(vi) Next, on the center of each vertical break-lines, one additional break-line is drawn and the procedures (ii) to (v) are repeated.
(vii) In this manner, the recorded diagram is divided by 2 m, and a sequential line graph is drawn, the transversal axis of the graph representing $1/\lambda$ corresponding roughness frequency, the vertical axis of the graph representing H and $H/\lambda$.
(viii) If a sequential line graph is determined by (vii) in accordance with the measured number for one ship or steel plate, the average profile is drawn as a whole and taken as H and $H/\lambda$ to the apparent wavelength $\lambda$.

As described above, the apparent wave height H and the apparent wave length $\lambda$ are different from the roughness height R determined and the average length RSm of roughness profile elements in JIS. Moreover, the non-patent document 2 discloses that a specimen steel plate having a length of 3 m, a width of 0.7 m width and a thickness of 6 mm was subjected to a towing tank test for confirmation of the same tendency, but the maximum speed was limited to 6 (m/s) and the influence due to the roughness parameter was not confirmed.

Thus, it discloses the relationship between the frictional resistance and the surface roughness, but does not disclose a method of estimating the frictional resistance by the surface roughness with a high reliability.

CITATION LIST

Non-Patent Document

Non-patent document 1: D. Byrne; "Hull roughness and the impact of outer hull maintenance decisions on ship efficiency", The First International Ship Repair, Spares and Maintenance Conference (1983) p 33-51

Non-patent document 2: SASAJIMA Hideo, TERAO Teiichi, YOKOO Koichi, NAKATO Michio and OGAWA Akihiro "Experimental study for Hull outer plate roughness and frictional resistance increase" Journal of the Society of Naval Architects of Japan Vol. 117, pp 58-71, 1965-06

SUMMARY OF THE INVENTION

Problems to be Solved by the Invention

Generally, the increase of a frictional resistance due to a surface roughness in an actual ship is the most practically estimated by the measurement of a horsepower. In practical running conditions, the increase thereof also depends on other influences such as wave-making resistance, wind, wave, tidal current, ship bottom fouling and the like, and thereby it is difficult to evaluate by choosing only the influence due to frictional resistance. With regard to data of surface roughness in coating films coated on a shell plating, evaluating by the maximum height in an evaluation length of 50 mm developed by BSRA prevails. However, it has a problem such that only the maximum height in a length of 50 mm is measured and thereby the influences due to other parameters cannot be evaluated. There are examples that the increase rate of a frictional resistance in an actual ship is shown by parameters of a height and a wave length, or a height and a gradient, but the optimum evaluation method, the evaluation length and cut-off wave-length are not determined in the case of an actual ship.

Since the evaluation of the frictional resistance in an actual ship is difficult as described above, it is necessary to estimate the frictional resistance simply and easily by another method for evaluating the frictional resistance in place of that. However, in a roughness that will correspond to that an actual ship has, measuring methods, by which an increase in frictional resistance that will correspond to that exhibited by an actual ship is exhibited, are limited. It is important to estimate the increase of an resistance corresponding to an actual ship by the proper combined use of a roughness measuring method and a frictional resistance measuring method.

Means for Solving the Problems

Under the circumstances, the present inventors have studied on a simple and optimum method of evaluating the coating film of an actual ship.

As a result, the inventors have found that the frictional resistance of a coating film of a ship can be estimated by the following structures. Thus the present invention has been accomplished.

[1] A method of estimating a frictional resistance of a ship bottom coating film, the method comprising: measuring any one of Rz (maximum height roughness), Rc (mean height of roughness profile elements), Ra (arithmetic mean roughness), Rq (root mean square roughness) and RZJIS (ten-point mean roughness) as a roughness height R in a mean length RSm of roughness profile elements in the range of 2,000 to 10,000 μm according to the rule defined in JIS B 0601:2001 (ISO4287:1997) on a coating film formed by applying a ship bottom coating paint on a substrate; and calculating a frictional resistance increase rate FIR (%) from a mirror surface by the following formula (4):

$$FIR(\%) = C\frac{R^2}{RSm} \quad (4)$$

wherein coefficient C is a constant depending on the kind of the roughness height R and a frictional resistance testing method, and is previously determined in such a manner that plural ship bottom coating films each having different roughness are subjected to a roughness measurement and a frictional resistance test in a definite evaluation length, and then the coefficient C is determined by the formula (4) using the roughness height R, the mean length RSm of roughness profile elements and the frictional resistance increase rate FIR (%), which have been measured.

[2] The method of estimating a frictional resistance of a ship bottom coating film according to the item [1], wherein the roughness is measured in an evaluation length of 10,000 μm or more, and in a measurement pitch of 500 μm or less, in the rule defined in JIS B 0601:2001 (ISO 4287:1997).

[3] The method of estimating a frictional resistance of a ship bottom coating film according to the item [2], wherein the roughness is measured by use of a high-pass filter such that the cut-off value λc is 10,000 μm or more.

[4] The method of estimating a frictional resistance of a ship bottom coating film according to any one of the items [1] to [3], wherein the frictional resistance test uses a double cylinder device, and comprises firstly determining a torque $T_0$, which acts on an internal cylinder with a mirror surface when an external cylinder is rotated, then determining a torque T, which acts on the internal cylinder coated with a ship bottom coating paint when the rotation is carried out under the same condition, and determining the frictional resistance increase rate FIR (%) by the following formula (5):

$$FIR(\%) = \frac{T - T_0}{T_0} \times 100 \quad (5)$$

and wherein the coefficient C is previously determined by the formula (4) that describes the relationship between the roughness height R and the mean length RSm of roughness profile elements of the coating film applied on the internal cylinder.

[5] The method of estimating a frictional resistance of a ship bottom coating film according to any one of the items [1] to [4], wherein the roughness height R and the mean length RSm of roughness profile elements are measured by a stylus type roughness measuring device or a laser displacement type roughness measuring device.

[6] A method of evaluating coating film performance of a ship bottom coating film, the method comprising using a coefficient C which has been previously determined, measuring a roughness height R and a mean length RSm of roughness profile elements with regard to a coating film formed by applying a ship bottom coating paint on a substrate, and estimating a frictional resistance increase rate FIR (%) by the formula (1).

[7] The method of evaluating coating film performance of a ship bottom coating film according to the item [6], wherein the roughness height R and the mean length RSm of roughness profile elements are evaluated on a thermoplastic resin replica prepared by taking from an actual ship coating film.

[8] A device for evaluating coating film performance of a ship bottom coating film, the device being for evaluating coating film performance of an actual ship coating film, and comprising a measuring part for measuring a roughness height R and a mean length RSm of roughness profile elements and a frictional resistance calculating part for calculating a frictional resistance increase rate FIR (%) by using the formula (4).

Effects of the Invention

According to the present invention, the frictional resistance increase rate of a coated film of a ship bottom can be estimated by a very simple method of just evaluating the roughness. This method can apply to a quick selection of an antifouling coating paint having a lower frictional resistance, a determination on good or bad coating, understanding on a performance of a coating equipment and so on. Moreover, this method can be used to a control of coating application of an antifouling coating paint for an actual ship in a dockyard. The present invention also provides an evaluating device used for the method. The evaluation device can be made economically because the measuring conditions can be fixed by limiting the wavelength range of the roughness.

BRIEF DESCRIPTION OF DRAWING

FIG. 4 shows a roughness distribution of a bottom film of an actual ship (a replica method/evaluation length 30 mm).

EMBODIMENT FOR CARRYING OUT THE INVENTION

Figure 1:
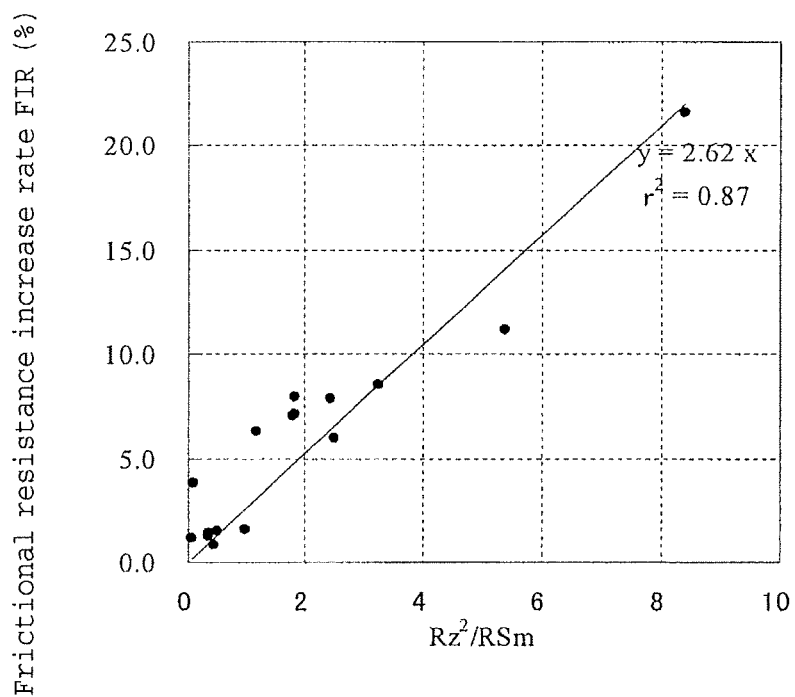
FIG. 1 shows a relationship between a frictional resistance increase rate FIR (%) and $Rz^2/RSm$.

The present invention will be described in detail below.
The coating paint for a ship bottom which paint is evaluated in the present invention is a coating paint used for corrosion prevention, prevention of organism adhesion and the like in a ship bottom. The coating paint is mainly a coating paint for a ship bottom of a steel ship.

The present invention may apply to these antifouling coating paints such as a self-polishing type antifouling coating paint and a fouling release type antifouling coating paint.

Regarding to the self-polishing type antifouling coating paint, the coating film is dissolved little by little gradually and simultaneously an antifouling agent which is a component having a distaste for aquatic life is also eluted to prevent adhesion of aquatic organism from the film. Regarding to the fouling release type antifouling coating paint, a coating film having smoothness, water repellency and elasticity makes adhesion of aquatic organisms harder.

Examples of the antifouling coating paints are coating paints disclosed in JP-B-4884107, JP-B-4846093, JP-B-4837668, JP-B-4813608, JP-B-4812947, JP-B-4812902, JP-B-4812895, JP-B-4806769, JP-B-4786053, JP-B-4777591, JP-B-4776839, JP-B-4769331, JP-B-4745351, JP-B-4709370, JP-B-4694583, JP-B-4684465, JP-B-4675624, JP-B-4651792, JP-B-4647060, JP-B-4644238, JP-B-4642204, JP-B-4641563, JP-B-4633224, JP-B-4621901 and JP-B-4610763. These known coating paints can be used without limitation.

In the present invention, the evaluation is carried out on a coating film formed by applying the coating paint for a ship bottom on a substrate.

The substrate is not particularly limited. Usual examples of the substrate are steels such as untreated steels, blast-treated steels, acid-treated steels, zinc-plated steels, and stainless steels; nonferrous metal materials such as aluminum (alloy) materials and copper (alloy) materials; concretes; and plastic materials such as vinyl chloride and the like. The shape of the substrate is not also particularly limited. Usually, a cylinder shape, a boat-like shape, a flat plate-like shape and a tube-like shape are used for evaluation.

The coating film for a ship bottom is formed by applying an antifouling coating paint on the surface of a substrate in accordance with a usual method and then, if necessary, vaporizing and removing a solvent at an ordinary temperature or under heating. The coating method is not particularly limited. Examples of the method are conventionally known methods such as an immersing method, a spray method, a brush application, a roller application, an electrostatic application and an electrodeposition application. The spray method is more preferably used to coat a wide ship bottom uniformly.

The film thickness is not particularly limited. The film may have a prescribed thickness. The film has a usual thickness of from 50 micron meter to 1,000 micron meter, such that the substrate is not shown and the roughness of the substrate surface is not affected.

Frictional Resistance Estimating Method

Regarding a coating film formed by applying a coating paint for ship bottom on a substrate, any of Rz (maximum height roughness), Rc (mean height of the roughness profile elements), Ra (arithmetical mean roughness), Rq (root mean square roughness) and RZJIS (ten-point mean roughness) in a mean length RSm of roughness profile elements in the range of 2,000 to 10,000 μm is measured in accordance with the rule defined in JIS B 0601:2001 (ISO4287: 1997) and the frictional resistance increase rate FIR (%) from a mirror surface is calculated by the following formula (4).

$$FIR(\%) = C \frac{R^2}{RSm} \tag{4}$$

In the formula, constant C depends on the kind of the roughness height R and a frictional resistance testing method and is previously determined in such a manner that a roughness measurement and a frictional resistance test in a definite evaluation length are carried out, and then the constant C is determined by the formula (4) using the roughness height R, the mean length RSm of roughness profile elements and the frictional resistance increase rate FIR (%), which have been measured.

RSm is a mean length of roughness profile elements and is represented by the following formula (6) as the mean of each length XS of roughness profile element.

$$RSm = \frac{1}{m}\sum_{i=1}^{n} Xsi \qquad (6)$$

Rz represents a maximum height roughness and is defined as the sum of the maximum profile peak height and the maximum profile valley depth in a standard length of a roughness profile. Rc represents a mean height of the roughness profile elements, Ra represents an arithmetical mean roughness and Rq represents a root mean square roughness. RZJIS represents a ten-point mean roughness and is defined as the sum of the mean heights of the five highest profile peaks and the mean depths of the five deepest profile valleys. These values are measured in accordance with the rule of JIS B 0601:2001 (ISO 4287:1997)

In evaluating the roughness in the present invention, it is only necessary to measure any one of the Rz (maximum height roughness), Rc (mean height of roughness profile elements), Ra (arithmetical mean roughness), Rq (root mean square roughness) and RZJIS (ten-point mean roughness).

These roughness measurements are conducted by using a contact type, a non-contact type, a manual type or an automatic type surface roughness measuring device. Furthermore, a stylus type or a laser displacement type surface roughness measuring device is preferably used in the standpoint of versatility and easy-to-use.

The resulting data may be saved or analog/digital-treated in the inside of a displacement instrument. For the measurement of the objective roughness, the evaluation length is not less than 10,000 μm, and the measurement pitch is not more than 500 μm in the present invention.

In the parameter analysis, it is desired to use the primary profile as it is. When a waviness having a wavelength of not less than 10,000 μm has an affect on the measurement, the roughness profile can be determined by including a high pass filter having a cut-off value (wavelength) λc of not less than 10,000 μm in accordance with JIS B 0601: 2001 (ISO 4287: 1997).

In the present invention, the necessary evaluation length and cut-off value λc for the accurate roughness evaluation are not less than 10,000 μm and the measurement pitch is not more than 500 μm. Furthermore, when the measurement pitch is 500 μm, the measurable minimum wavelength is 2,000 μm but the measurement error of the low wavelength roughness is large. Therefore, the practical measurement pitch is about 250 μm. When the measurement pitch is smaller, the measurement takes a longer period of time and influences on the wavelength of the low roughness height which is not related to the frictional resistance increase. Therefore, the measurement distance is preferably not less than 100 μm in the practical use. Moreover, when the measurement distance is small, or further the apparent wavelength is small by the small roughness and the noise which do not contribute to the frictional resistance, cut by a low pass filter may be conducted.

Determination of Coefficient C

The gradient C in the formula (4) varies depending to the kind of the roughness height R and the frictional resistance test method. Previously, plural ship bottom coating films each having different roughness are formed on prescribed substrates and then evaluated on frictional resistance thereof by the frictional resistance test to determine the coefficient C in the formula (4). For example, when Rz and RSm are measured in an evaluation length of 50 mm and the frictional resistance test is carried out using a double cylinder device, the coefficient C is about 2 to 3. The frictional resistance test is necessary to be conducted by a method of showing a frictional resistance increase rate of not less than 5% on a coating film having a roughness height R of 100 μm and RSm of 2,000 to 4,000 μm, which are determined by the above roughness measuring method.

Because this is a frictional resistance increase rate under the condition of a high Reynolds number and a thin viscous sublayer thickness, which correspond to an actual ship, and the tank towing test and the flowing round tank test, which are generally used to ship evaluation, are not appropriate because the velocity is low and the length of a test plate is short and thereby the roughness is in hiding under a viscous sublayer, and as a result, the influence of the roughness is not exerted sufficiently.

In order to realize the viscous sublayer thickness which corresponds to an actual ship, it is preferred to employ a method such that the distance between a main flow and the surface of a wall is short and the flow rate is as rapid as possible. The test capable of yielding these results are conducted by a double cylinder device, an in-pipe flow path or a cavitation water tank.

In the case that the double cylinder device is used, a torque $T_0$, which acts on an internal cylinder with a mirror surface when an external cylinder is rotated at a prescribed rotation number, is determined, then, a torque T, which acts on the internal cylinder coated with a ship bottom coating paint when the rotation is carried out in the same conditions, is determined, and the frictional resistance increase rate FIR (%) is measured by the following formula (5).

$$FIR(\%) = \frac{T - T_0}{T_0} \times 100 \qquad (5)$$

Next, from the formula (4) showing the relationship of the FIR (%) measured, and R and RSm of the coating film formed on the internal cylinder, the coefficient C is determined.

When the coefficient C is used to the formula (4) and R and RSm are measured, the frictional resistance increase rate of a coating film can be estimated regardless of the kind of the ship bottom coating paint.

As described above, the coefficient C previously determined is used, the roughness height R and the mean length RSm of roughness profile elements are measured with respect to a coating film formed by applying the ship bottom coating paint on a substrate, and then the frictional resistance increase rate FIR (%) is estimated by the formula (4). Thus, the coating film performance of the ship bottom coating film can be evaluated.

When in the ship coating job site of a dockyard, the surface roughness of a ship bottom coating film is measured in the following manner that a thermoplastic resin is pressed against a frame pattern to prepare a replica and the surface roughness is measured, the frictional resistance increase rate of the coating film of an actual ship can be estimated.

Specifically, in order to obtain the sufficient accuracy, the surface roughness of the coating film formed on the internal cylinder was measured by a laser displacement instrument on 10 lines, in which one line is spaced apart from another line at intervals of 25 mm, the measurement of the surface roughness on each line being begun at the lower part of the internal cylinder and continued to the upper part of the internal cylinder, except the part measuring 50 mm from the bottom part of the internal cylinder. The laser displacement instrument is installed on the test device and the cylinder is rotated and then the surface roughness is measured. The displacement data are obtained at intervals of 250 μm, and thereby 4,000 data are obtained in the distance of 1,000 mm. The measured data in one line are divided by 20 with an evaluation length of 50 mm and then an approximate profile with root mean square is subtracted from the above value to determine the primary profile.

The device of evaluating coating film performance of a ship bottom coating film according to the present invention, which is conducted by the above estimating method, comprises a measurement part for measuring the roughness height R and the mean length RSm of roughness profile elements, and a frictional resistance calculating part for calculating the frictional resistance increase rate FIR (%) using the formula (4).

The above described roughness measuring device is provided in the measuring part. In an estimating part, the resultant data are monitored and the frictional resistance increase rate can be estimated from the formula (4).

In the ship coating job site of a dockyard, the frictional resistance increase rate of a ship bottom coating film can be easily estimated by the use of this coating film performance evaluation device, and the coating film performance can be evaluated.

Moreover, as the wavelength range of the roughness is limited, the evaluation length, the measurement pitch and the cutoff value λc, which are the roughness measurement conditions, can be fixed. Therefore, the coating film capacity evaluation device can be provided at a low cost.

EXAMPLE

The present invention will be described in more detail with reference to the following examples below, and it should not be limited by the examples.

Example 1

Frictional Resistance Test (i) the Case of Using a Double Cylinder Device

The double cylinder device was used and the relationship of the roughness height R, the mean length RSm of roughness profile elements and the frictional resistance increase rate is evaluated.

In the double cylinder device, a polyvinyl chloride made test cylinder (internal cylinder 310 mm diameter) on which a coating paint was applied by spray coating was set in a stainless steel tank (external cylinder 320 mm diameter) filled with an ion exchanged water (23° C.).

Regarding to the coating paints, BANNOH 500N (manufactured by Chugoku Marine Paints Ltd.) was used as a binder coat, and SEA GRANDPRIX 500, SEA GRANDPRIX 1000, SEAFLO NEO or BIOCLEAN HB (all is manufactured by Chugoku Marine Paints Ltd.) was used as an antifouling coating paint. The total thicknesses of the coating films were 125 μm or 250 μm.

The external cylinder was rotated at 1000 rpm and a torque which acted on the internal cylinder on which the coating film was formed was measured. Subsequently, the frictional resistance increase rate FIR (%) was calculated, provided that a torque, which acted on a complete mirror surface when the external cylinder was rotated at 1000 rpm, was 6.55 N·m and 6.63 N·m when the film thickness was 125 μm and 250 μm, respectively.

The frictional resistance increase rate FIR (%) of the internal cylinder on which each coating film was formed was calculated by the formula (5). In the formula (5), $T_0$ is a torque which acted on the internal cylinder with a mirror surface when the external cylinder was rotated at 1000 rpm, and $T_0$ was 6.55 N·m and 6.63 N·m when the film thickness were 125 μm and 250 μm, respectively. T is a torque which acted on the internal cylinder coated with the ship bottom coating paint when the rotation was carried out in the same conditions.

The roughness measurement was carried out on the internal cylinder on which each coating film was formed.

In order to obtain sufficiently high accuracy, the surface roughness of the internal cylinder on which the coating film was formed was measured by a laser displacement instrument on 10 lines, in which one line is spaced apart from another line at intervals of 25 mm, the measurement of the surface roughness on each line being begun at the upper part of a specimen and continued to the lower part of the specimen, except the part measuring 50 mm from. The laser displacement instrument was installed on the double cylinder device and the internal cylinder on which the coating film was formed was rotated to measure the surface roughness. The displacement data were obtained at intervals of 250 μm and 4,000 data were obtained in the distance of 1,000 mm. The measured data on one line was divided by 20 in an evaluation length of 50 mm and then an approximate profile with the root mean square was subtracted to determine the primary profile.

With regard to the coating film formed by a spray coating, Rz (maximum height roughness) and RSm (mean length of roughness profile elements) were calculated and as a result, in the evaluation length of 50 mm, Rz was 30 μm to 200 μm and RSm was 2,000 μm to 10,000 μm. In order to evaluate the RSm range accurately, the necessary evaluation length and cut-off value λc are 10,000 μm or more and the measurement pitch is 500 μm or less. When the measurement distance is 500 μm, the measurable minimum wavelength is 2,000 μm, but an error of the measurement of Rz and RSm in a low wavelength will be large. Therefore, it is practically about 250 μm. Furthermore, when the measurement distance is small, the measurement time is longer. Therefore, it is practically and appropriately 100 μm or more. Moreover, when the measurement pitch is smaller, it is occasionally preferred to conduct cutting by a low pass filter because an apparent wavelength will become small by the influences of a small roughness which does not contribute the frictional resistance and a noise. In the practical evaluation, it is preferred to determine a roughness profile by introducing a low pass filter in a cut-off wavelength λs in order to remove the influence of a waviness of a long wavelength. However, in the precisely processed circular cylinder, the primary profile was evaluated as it was because the affect of a waviness of a long wavelength was not observed.

From the primary profile, Rz (maximum height roughness), Rc (mean height of roughness profile elements), Ra (arithmetic mean roughness), Rq (root mean square roughness), RZJIS (ten-point mean roughness) and RSm were calculated.

Figure 2:
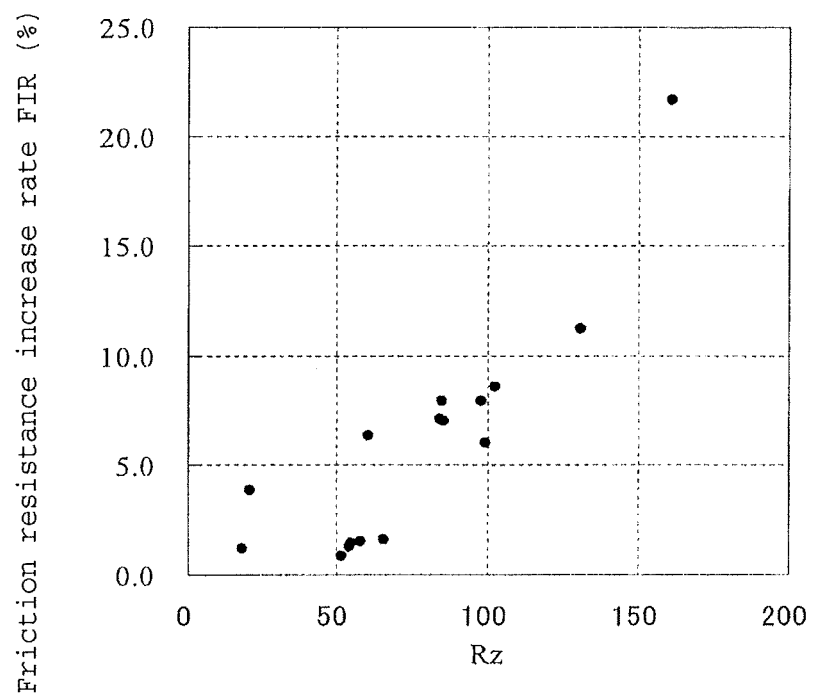
FIG. 2 shows a relationship between a frictional resistance increase rate FIR (%) and a maximum height roughness Rz.
Figure 3:
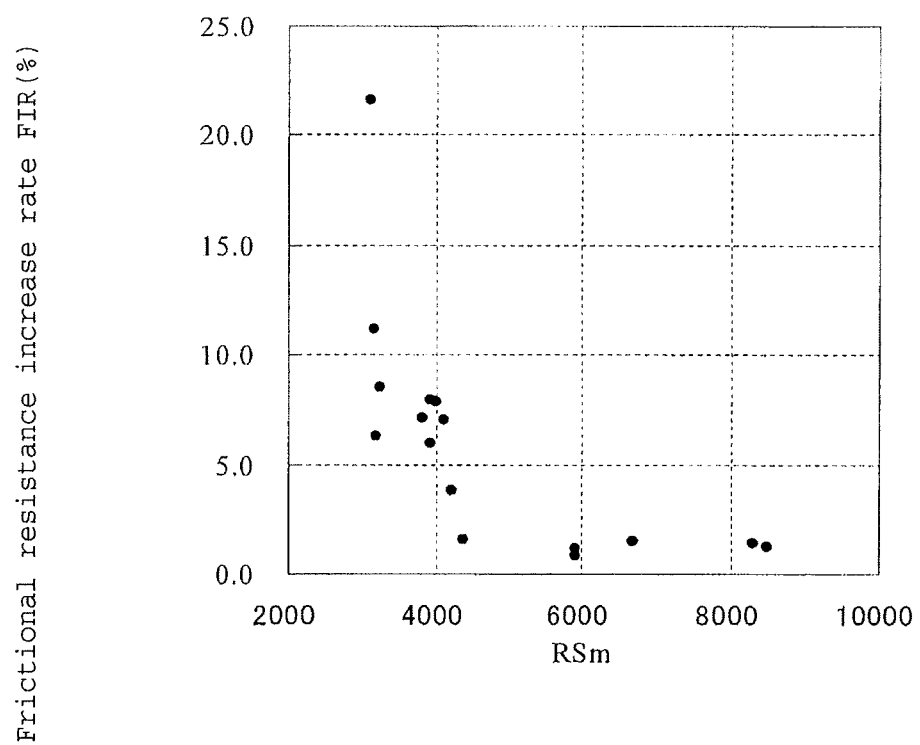
FIG. 3 shows a relationship between a frictional resistance increase rate and a mean length RSm of roughness profile elements.

In the case of the measurement using the double cylinder device, Rz, Rc, Ra, Rq, RZJIS and RSm, and the frictional resistance increase rate FIR (%) were shown in Table 1. The mutual correlation analysis on Rz, Rc, Ra, Rq, RZJIS and RSm was carried out and the results are shown in Table 2. As Rz, Rc, Ra, Rq and RZJIS show a high correlation mutually, the evaluation may be carried out using any one of the roughness heights R. In the case that the relationship of RSm, Rz and FIR (%) is evaluated, when the value $Rz^2/RSm$ obtained by dividing $Rz^2$ by RSm is taken as a transverse axis and FIR (%) is taken as a vertical axis, a high correlation is confirmed along an approximation straight line as shown in FIG. 1. However, when Rz or RSm is taken as a transverse axis and FIR (%) is taken as a vertical axis, large variation is observed as shown in FIG. 2 and FIG. 3. Therefore, it is preferred to estimate FIR (%) by $Rz^2/RSm$. In this example, the approximation line is a graph passing through the point 0 and having a gradient of 2.62. Accordingly, FIR (%) can be determined from Rz and RSm by calculating backwards from this numeral formula. As is shown in FIG. 2, Rc, Ra, Rq and RZJIS have a high correlation with Rz and thereby using any of them, the evaluation can be conducted in the same manner. But, the coefficient C has a different value in accordance with the kind of the roughness height R.

TABLE 1

Roughness height R, RSm, $Rz^2/RSm$ and frictional resistance increase rate FIR(%) (length for evaluation 50 mm)

| Maximum height roughness Rz (μm) | Mean height of roughness profile elements Rc (μm) | Arithmetic mean roughness Ra (μm) | Root mean square roughness Rq (μm) | Ten-point mean roughness Rzjis (μm) | Mean length of roughness profile elements RSm (μm) | $Rz^2$/RSm (μm) | Frictional resistance increase rate FIR (%) |
|---|---|---|---|---|---|---|---|
| 51.8 | 22.5 | 8.5 | 10.7 | 33.5 | 5914 | 0.45 | 0.80 |
| 18.4 | 7.1 | 3.2 | 3.9 | 11.1 | 5917 | 0.06 | 1.16 |
| 54.3 | 27.4 | 9.7 | 12.1 | 32.3 | 8506 | 0.35 | 1.21 |
| 55.0 | 27.6 | 9.9 | 12.3 | 33.6 | 8321 | 0.36 | 1.44 |
| 58.1 | 26.4 | 9.6 | 12.1 | 36.3 | 6694 | 0.50 | 1.46 |
| 66.2 | 25.7 | 9.8 | 12.7 | 43.6 | 4400 | 1.00 | 1.57 |
| 21.0 | 8.0 | 3.4 | 4.2 | 13.9 | 4225 | 0.10 | 3.79 |
| 99.5 | 42.9 | 15.5 | 19.5 | 71.3 | 3927 | 2.52 | 5.99 |
| 61.3 | 24.2 | 9.0 | 11.4 | 45.2 | 3173 | 1.18 | 6.30 |
| 86.2 | 35.5 | 13.0 | 16.6 | 59.9 | 4133 | 1.80 | 7.00 |
| 84.4 | 35.9 | 13.2 | 16.5 | 61.1 | 3838 | 1.86 | 7.09 |
| 98.7 | 42.4 | 15.4 | 19.4 | 71.0 | 4007 | 2.43 | 7.87 |
| 85.1 | 36.5 | 13.4 | 16.7 | 62.3 | 3927 | 1.84 | 7.93 |
| 103.0 | 43.0 | 15.8 | 19.8 | 76.9 | 3244 | 3.27 | 8.54 |
| 130.9 | 53.7 | 19.5 | 24.8 | 97 | 3167 | 5.41 | 11.18 |
| 161.3 | 63.4 | 22.8 | 29.6 | 116.1 | 3096 | 8.40 | 21.64 |

TABLE 2

Mutual correlation of roughness height R and RSm (length for evaluation 50 mm)

| | Rz (μm) | Rc (μm) | Ra (μm) | Rq (μm) | Rzjis (μm) | RSm (μm) |
|---|---|---|---|---|---|---|
| Rz (μm) | 1.00 | | | | | |
| Rc (μm) | 0.99 | 1.00 | | | | |
| Ra (μm) | 0.99 | 1.00 | 1.00 | | | |
| Rq (μm) | 1.00 | 1.00 | 1.00 | 1.00 | | |
| Rzjis (μm) | 1.00 | 0.98 | 0.99 | 0.99 | 1.00 | |
| RSm (μm) | −0.57 | −0.47 | −0.50 | −0.50 | −0.63 | 1.00 |

Example 2

Roughness Measurement of a Coating Film of an Actual Ship

With regard to actual ship bottoms (4 ships), Rz, Rc, Ra, Rq, RZJIS and RSm were measured and the results are shown in Table 3. On the ship bottoms of the 4 ships, antifouling paints (a) SEAFLONEO, (b) SEA GRANDPRIX 500HS, (c) SEA GRANDPRIX 500 and (d) SEA GRANDPRIX 1000 (any of the antifouling paints was manufactured by Chugoku Marine Paints, Ltd.) were applied respectively. A replica of roughness of each coating film was taken by a thermoplastic resin and carried back to the laboratory and surface roughness was measured by the laser displacement instrument. The evaluation range was 30 mm×30 mm, the measurement distance was 250 μm and the evaluation length was 30,000 μm. Through this measurement, the roughness profiles as shown in FIG. 4 were able to be measured. Rz, Rc, Ra, Rq, RZJIS and RSm were equal to those in Example 1. From this fact, the measurement in the range of RSm equal to that in Example 1 can be carried out on the coating film of the bottom of an actual ship.

TABLE 3

Surface roughness analysis example in an actual ship shell plating (Replica method/evaluation length 30 mm)

| | Rz: | Rc: | Ra: | Rq: | Rzjis: | RSm: |
|---|---|---|---|---|---|---|
| 1)-1 | 43.6 | 21.0 | 7.8 | 9.6 | 24.3 | 4798 |
| 1)-2 | 60.1 | 23.7 | 10.2 | 12.7 | 30.9 | 4811 |

TABLE 3-continued

Surface roughness analysis example in an actual ship shell plating (Replica method/evaluation length 30 mm)

| | | | | | | |
|---|---|---|---|---|---|---|
| 1)-3 | 53.7 | 28.1 | 9.6 | 11.9 | 26.6 | 4809 |
| 1)-4 | 52.3 | 14.1 | 8.5 | 10.7 | 26.1 | 4198 |
| 1)-5 | 71.1 | 25.3 | 12.8 | 15.8 | 39.9 | 4289 |
| 1)-6 | 55.4 | 11.3 | 9.0 | 11.3 | 25.4 | 5118 |
| 1)-7 | 57.0 | 15.7 | 10.0 | 12.3 | 28.0 | 4870 |
| 1)-8 | 78.2 | 23.7 | 11.0 | 14.6 | 35.5 | 5279 |
| 1)-9 | 53.8 | 22.2 | 10.1 | 12.2 | 27.8 | 6014 |
| 1)-10 | 52.1 | 18.7 | 9.6 | 11.6 | 29.1 | 4211 |
| 1)-11 | 72.9 | 17.5 | 12.7 | 16.0 | 31.6 | 6040 |
| 1)-12 | 67.3 | 13.2 | 11.9 | 14.9 | 29.5 | 4479 |
| 1)-13 | 73.2 | 25.2 | 12.3 | 15.3 | 38.6 | 4466 |
| 1)-14 | 65.6 | 18.9 | 11.4 | 14.2 | 30.0 | 4947 |
| 1)-15 | 54.5 | 31.2 | 9.8 | 12.0 | 28.9 | 5309 |
| Mean | 60.7 | 20.7 | 10.4 | 13.0 | 30.2 | 4909 |

| | Rz: | Rc: | Ra: | Rq: | Rzjis: | Sm: |
|---|---|---|---|---|---|---|
| 2)-1 | 120.0 | 50.0 | 21.8 | 27.0 | 47.7 | 4727 |
| 2)-2 | 109.3 | 35.8 | 17.4 | 21.9 | 68.1 | 3228 |
| 2)-3 | 76.8 | 22.8 | 13.0 | 16.1 | 45.0 | 3414 |
| 2)-4 | 65.2 | 12.6 | 11.9 | 14.6 | 39.8 | 3762 |
| 2)-5 | 72.5 | 21.3 | 13.0 | 16.0 | 46.9 | 4094 |
| 2)-6 | 64.6 | 33.2 | 11.5 | 14.2 | 38.5 | 4098 |
| 2)-7 | 79.3 | 37.1 | 14.0 | 17.3 | 47.7 | 3832 |
| 2)-8 | 55.3 | 19.3 | 9.1 | 11.2 | 34.4 | 3407 |
| 2)-9 | 64.6 | 33.2 | 11.5 | 14.2 | 38.5 | 4098 |
| 2)-10 | 101.3 | 35.7 | 16.0 | 20.2 | 68.9 | 2823 |
| 2)-11 | 68.6 | 17.4 | 11.0 | 13.9 | 38.0 | 3087 |
| 2)-12 | 64.1 | 34.1 | 10.2 | 12.8 | 41.4 | 2784 |
| 2)-13 | 94.9 | 29.5 | 16.0 | 19.9 | 58.2 | 3263 |
| 2)-14 | 101.3 | 35.7 | 16.0 | 20.2 | 68.9 | 2823 |
| 2)-15 | 63.6 | 30.3 | 10.1 | 12.7 | 42.5 | 2775 |
| Mean | 80.1 | 29.9 | 13.5 | 16.8 | 48.3 | 3481 |
| 3)-1 | 74.9 | 20.4 | 13.0 | 16.2 | 32.7 | 4318 |
| 3)-2 | 73.4 | 29.4 | 12.2 | 15.2 | 38.0 | 3854 |
| 3)-3 | 95.2 | 44.8 | 16.2 | 20.3 | 57.9 | 3579 |
| 3)-4 | 107.4 | 29.2 | 19.3 | 23.8 | 65.2 | 3488 |
| 3)-5 | 109.4 | 60.6 | 20.5 | 25.2 | 46.6 | 4082 |
| 3)-6 | 75.8 | 57.7 | 12.5 | 15.7 | 46.0 | 3476 |
| 3)-7 | 80.9 | 23.5 | 11.8 | 15.1 | 44.0 | 3636 |
| 3)-8 | 109.1 | 44.7 | 18.8 | 23.2 | 52.2 | 4764 |
| 3)-9 | 103.7 | 37.0 | 16.7 | 21.1 | 61.7 | 3330 |
| 3)-10 | 68.8 | 32.8 | 11.5 | 14.4 | 42.3 | 3537 |
| 3)-11 | 59.3 | 15.3 | 10.0 | 12.3 | 32.2 | 3336 |
| 3)-12 | 89.1 | 84.8 | 15.6 | 19.1 | 50.1 | 3144 |
| Mean | 89.9 | 38.0 | 15.2 | 19.0 | 48.7 | 3806 |
| 4)-1 | 82.7 | 44.6 | 14.1 | 17.5 | 54.6 | 3733 |
| 4)-2 | 99.8 | 45.1 | 18.0 | 22.3 | 57.3 | 5134 |
| 4)-3 | 55.5 | 26.3 | 9.7 | 12.0 | 34.1 | 3613 |
| 4)-4 | 60.6 | 35.1 | 10.7 | 13.3 | 34.6 | 4643 |
| 4)-5 | 76.9 | 65.7 | 14.9 | 18.2 | 33.8 | 7592 |
| 4)-6 | 107.4 | 32.4 | 16.4 | 21.2 | 48.4 | 4231 |
| 4)-7 | 82.8 | 47.5 | 14.1 | 17.4 | 55.9 | 2597 |
| 4)-8 | 75.8 | 15.6 | 14.1 | 17.2 | 42.0 | 3337 |
| 4)-9 | 75.4 | 47.0 | 13.9 | 16.9 | 45.9 | 4876 |
| Mean | 79.7 | 39.9 | 14.0 | 17.3 | 45.2 | 4417 |

1) . . . (a) SEAFLO NEO
2) . . . (b) SEA GRANDPRIX 500HS
3) . . . (c) SEA GRANDPRIX 500
4) . . . (d) SEA GRANDPRIX 1000

Figure 5:
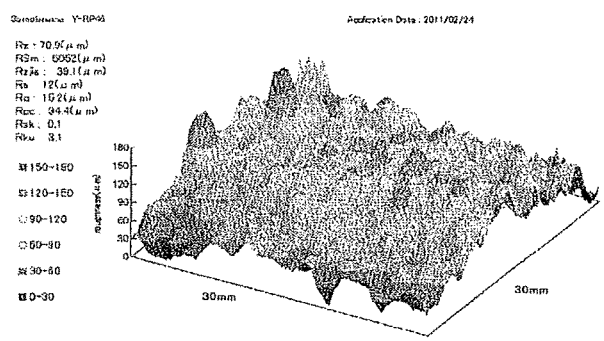
FIG. 5 shows an example of roughness acquisition of a bottom film of an actual ship.
Figure 6:
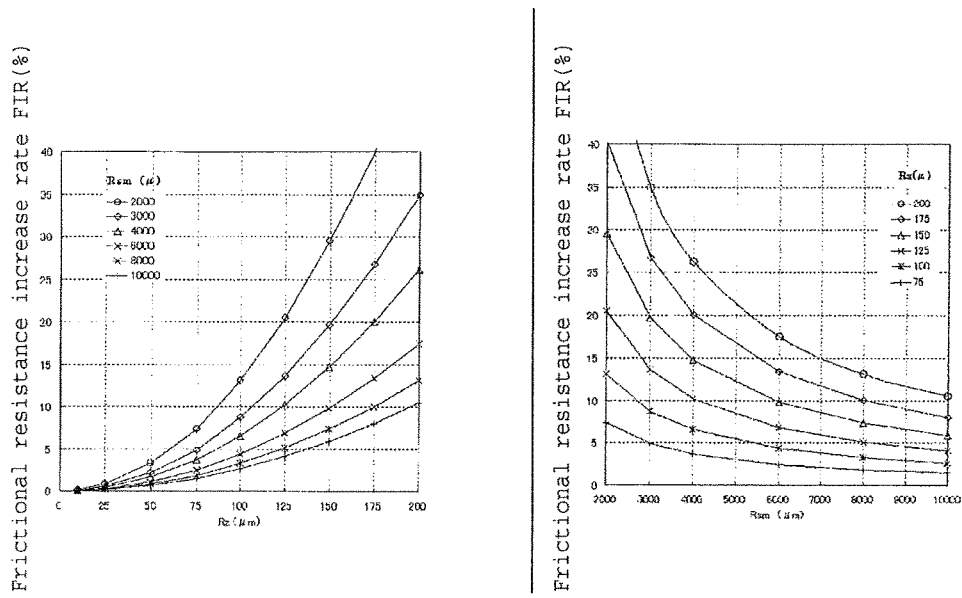
FIG. 6 shows an estimation example (FIR (%)=$2.62 \times Rz^2/RSm$) of a frictional resistance increase rate FIR (%).

In FIG. 5, the values Rz and RSm are shown by three-dimensional column graph. From the result, it was found that the roughness of the shell plating can be evaluated by the method of the present invention. Furthermore, from the mean values Rz and RSm of each ship, the estimation value of FIR (%) was calculated using the coefficient C of 2.62.

Example 3

A Method of Estimating the Frictional Resistance Increase Rate

The estimation example of the frictional resistance increase rate obtained in Example 1 are shown in Table 6. When FIR (%) was calculated using the coefficient C of 2.62, it is confirmed there is a tendency such that as Rz is larger and RSm is smaller, FIR (%) is larger. From these figures, it can be easily estimated to the roughness range in which FIR (%) increases remarkably. Furthermore, Rz and RSm are introduced into the estimation formula directly and thereby the difference of FIR (%) can be compared.

The invention claimed is:

1. A method of estimating a frictional resistance of a coating film, the method comprising:
   measuring a roughness height R of a coating film painted on a substrate in an area having a mean length of roughness profile elements RSm of 2,000 to 10,000 µm according to JIS B 0601:2001 (ISO4287:1997), wherein the roughness height R of the coating film is at least one selected from the group consisting of a maximum height roughness Rz, a mean height of roughness profile elements Rc, an arithmetic mean roughness Ra, a root mean square roughness Rq, and a ten-point mean roughness RZJIS; and
   calculating a frictional resistance increase rate FIR (%) of the coating film with respect to a mirror surface by formula (1);

$$FIR(\%) = C\frac{R^2}{RSm}, \tag{1}$$

wherein coefficient C is a constant predetermined by measuring a roughness within a fixed length of a plurality of test coating films having different roughness to determine a roughness height R and a mean length of roughness profile elements RSm of each of the test coating films, conducting a frictional resistant test on each of the test coating films to obtain a frictional resistance increase rate FIR (%) with respect to a mirror surface for each of the test coating films, and calculating the coefficient C from the roughness height R, the mean length of roughness profile elements RSm, and the frictional resistance increase rate FIR of the test coating films by the formula (1),
wherein the roughness height R of the test coating films measured to predetermine the coefficient C is at least one selected from the group consisting of a maximum height roughness Rz, a mean height of roughness profile elements Rc, an arithmetic mean roughness Ra, a root mean square roughness Rq, and a ten-point mean roughness RZJIS, of the test coating films,
wherein the coefficient C depends on the kind of the roughness height R and the frictional resistance test conducted to predetermine the coefficient C, and
wherein the frictional resistant test to predetermine the coefficient C is carried out by using at least one of a double cylinder device, an in-pipe flow path, and a cavitation water tank.

2. The method according to claim 1, wherein the measuring of the roughness height R is conducted in an evaluation length of 10,000 μm or more, and a measurement pitch of 500 μm or less according to JIS B 0601:2001 (ISO 4287:1997).

3. The method according to claim 2, wherein the measuring of the roughness height R is conducted by using a high pass filter such that the cut-off value λc is 10,000 μm or more.

4. The method according to claim 1, wherein, in predetermining the coefficient C, the frictional resistance test is carried out by using a double cylinder device by rotating an external cylinder of the double cylinder device to determine a torque $T_0$ which works on an internal cylinder of the double cylinder device having a mirror surface and then rotating the external cylinder under the same rotating condition to determine a torque T which works on an internal cylinder on which each of the test coating films is formed, and the frictional resistance increase rate FIR (%) of the test coating films is determined from formula (2):

$$FIR(\%) = \frac{T - T_0}{T_0} \times 100. \quad (2)$$

5. The method according to claim 1, wherein, in the measuring, the roughness height R and the mean length of roughness profile elements RSm are measured by a stylus type roughness measurement device or a laser displacement type roughness measurement device.

6. A method of evaluating performance of a coating film, the method comprising:
measuring a roughness height R and a mean length of roughness profile elements RSm; and
estimating a frictional resistance increase rate FIR (%) by the formula (1);

$$FIR(\%) = C\frac{R^2}{RSm}, \quad (1)$$

wherein C is a coefficient predetermined with regard to a coating film formed by applying a coating paint on a substrate, and
wherein the coefficient C is predetermined by a frictional resistant test using at least one of a double cylinder device, an in-pipe flow path, and a cavitation water tank.

7. The method according to claim 6, wherein the roughness height R and the mean length of roughness profile elements RSm are measured on a thermoplastic resin replica taken from an actual ship coating film.

8. A device for evaluating a performance of an actual ship coating film, the device comprising:
a stylus type roughness measurement device or a laser displacement type roughness measurement device for measuring a roughness height R and a mean length of roughness profile elements RSm; and
a frictional resistance calculating part for calculating a frictional resistance increase rate FIR (%) by the formula (1):

$$FIR(\%) = C\frac{R^2}{RSm}. \quad (1)$$

9. The method according to claim 1, wherein the coating film painted on a substrate is a coating film formed on a ship bottom.

10. The method according to claim 6, wherein the coating film is a coating film formed on a ship bottom.

11. The method according to claim 1, wherein the measuring comprises measuring a maximum height roughness Rz of the coating film.

12. The method according to claim 1, wherein the measuring comprises measuring a mean height of roughness profile elements Rc of the coating film.

13. The method according to claim 1, wherein the measuring comprises measuring an arithmetic mean roughness Ra of the coating film.

14. The method according to claim 1, wherein the measuring comprises measuring a root mean square roughness Rq of the coating film.

15. The method according to claim 1, wherein the measuring comprises measuring a ten-point mean roughness RZJIS of the coating film.

16. The method according to claim 1, wherein the measuring comprises measuring a mean length of roughness profile elements RSm of the coating film such that the area having a mean length of roughness profile elements RSm of 2,000 to 10,000 μm is determined.

17. A method of estimating a frictional resistance of a coating film, the method comprising:
measuring a roughness height R of a coating film painted on a substrate in an area having a mean length of roughness profile elements RSm of 2,000 to 10,000 μm according to JIS B 0601:2001 (ISO4287:1997), wherein the roughness height R of the coating film is at least one selected from the group consisting of a maximum height roughness Rz, a mean height of roughness profile elements Rc, an arithmetic mean roughness Ra, a root mean square roughness Rq, and a ten-point mean roughness RZJIS, and wherein the roughness height R and the mean length of roughness profile elements RSm are measured by a stylus type roughness measurement device or a laser displacement type roughness measurement device; and
calculating a frictional resistance increase rate FIR (%) of the coating film with respect to a mirror surface by formula (1);

$$FIR(\%) = C\frac{R^2}{RSm}, \quad (1)$$

wherein coefficient C is a constant predetermined by measuring a roughness within a fixed length of a plurality of test coating films having different roughness to determine a roughness height R and a mean length of roughness profile elements RSm of each of the test coating films, conducting a frictional resistant test on each of the test coating films to obtain a frictional resistance increase rate FIR (%) with respect to a mirror surface for each of the test coating films, and calculating the coefficient C from the roughness height R, the mean length of roughness profile elements RSm, and the frictional resistance increase rate FIR of the test coating films by the formula (1),
wherein the roughness height R of the test coating films measured to predetermine the coefficient C is at least one selected from the group consisting of a maximum height roughness Rz, a mean height of roughness profile elements Rc, an arithmetic mean roughness Ra, a root mean square roughness Rq, and a ten-point mean roughness RZJIS, of the test coating films, and wherein the coefficient C depends on the kind of the roughness height R and the frictional resistance test conducted to predetermine the coefficient C.

18. The method according to claim 17, wherein the measuring of the roughness height R is conducted in an evaluation length of 10,000 μm or more, and a measurement pitch of 500 μm or less according to JIS B 0601:2001 (ISO 4287:1997).

19. The method according to claim 18, wherein the measuring of the roughness height R is conducted by using a high pass filter such that the cut-off value λc is 10,000 μm or more.

20. The method according to claim 17, wherein the coating film painted on a substrate is a coating film formed on a ship bottom.

* * * * *